(12) United States Patent
Bissey-Beugras et al.

(10) Patent No.: US 7,776,318 B2
(45) Date of Patent: Aug. 17, 2010

(54) LIQUID CLEANING COMPOSITION COMPRISING AT LEAST ONE ANIONIC SURFACTANT AND ITS USE FOR CLEANSING HUMAN KERATIN MATERIALS

(75) Inventors: Laure Bissey-Beugras, Levallois Perret (FR); Delphine Ribery, Levallois Perret (FR)

(73) Assignee: L'Oreal S.A., Paris (FR)

( * ) Notice: Subject to any disclaimer, the term of this patent is extended or adjusted under 35 U.S.C. 154(b) by 386 days.

(21) Appl. No.: 11/287,300

(22) Filed: Nov. 28, 2005

(65) Prior Publication Data

US 2006/0135397 A1 Jun. 22, 2006

Related U.S. Application Data

(60) Provisional application No. 60/634,542, filed on Dec. 10, 2004.

(30) Foreign Application Priority Data

Nov. 26, 2004 (FR) .................................. 04 52780

(51) Int. Cl.
C11D 1/02 (2006.01)
C11D 3/37 (2006.01)
C11D 7/10 (2006.01)

(52) U.S. Cl. .............. 424/70.16; 424/70.19; 424/70.21; 424/70.24; 424/70.31; 510/119; 510/123; 510/127; 510/155; 510/156; 510/159; 510/426; 510/434; 510/476; 510/490

(58) Field of Classification Search ................ 510/119, 510/123, 127, 155, 156, 159, 426, 434, 476, 510/490; 424/70.16, 70.19, 70.21, 70.24, 424/70.31
See application file for complete search history.

(56) References Cited

U.S. PATENT DOCUMENTS

| 4,310,432 | A | 1/1982 | Brouwer |
| 4,310,433 | A | 1/1982 | Stiros |
| 4,387,040 | A | 6/1983 | Straw |
| 5,507,971 | A | 4/1996 | Ouzounis et al. |
| 5,550,225 | A | 8/1996 | Philippe |
| 6,391,863 | B1 | 5/2002 | Philippe et al. |
| 6,743,760 | B1 | 6/2004 | Hardy et al. |
| 2003/0103926 | A1 | 6/2003 | Maubru |
| 2003/0108503 | A1 | 6/2003 | Maubru |
| 2003/0108578 | A1* | 6/2003 | Maubru ............... 424/401 |
| 2003/0147842 | A1 | 8/2003 | Restle et al. |
| 2003/0152542 | A1 | 8/2003 | Decoster et al. |
| 2003/0171230 | A1 | 9/2003 | Shana'a et al. |
| 2004/0023820 | A1 | 2/2004 | Patel |
| 2004/0234485 | A1* | 11/2004 | Maubru et al. ........ 424/70.16 |
| 2004/0265261 | A1 | 12/2004 | Kohut et al. |
| 2006/0120986 | A1 | 6/2006 | Albrecht et al. |

FOREIGN PATENT DOCUMENTS

| EP | 0 013 836 | | 8/1980 |
| EP | 0 459 077 | | 12/1991 |
| EP | 0 566 438 | | 10/1993 |
| EP | 1 312 333 | | 5/2003 |
| EP | 1 312 355 A1 | | 5/2003 |
| EP | 1 470 813 A2 | | 10/2004 |
| EP | 1 510 204 A1 | | 3/2005 |
| FR | 2 739 556 | | 4/1997 |
| JP | 3-34915 | | 2/1991 |
| JP | 4-169 519 | | 6/1992 |
| JP | 2003-516333 | | 5/2003 |
| WO | WO 01-41720 | | 6/2001 |
| WO | WO 01/76552 | * | 10/2001 |
| WO | WO 03/028683 A1 | | 4/2003 |
| WO | WO 2004/006870 A2 | | 1/2004 |
| WO | WO 2004/014333 A1 | | 2/2004 |
| WO | WO 2005/023969 | | 3/2005 |
| WO | WO 2005/087185 | | 9/2005 |

OTHER PUBLICATIONS

Dyer, "Comparison of Detergent Based Versus Soap Based Liquid Soaps", *Soap/Cosmetics/Chemical Specialties*, pp. 36-40 (1983).
Frank, "Formulation Technology of Liquid Soaps", *Cosmetics & Toiletries*, 97:49-54 (1982).
Hart, "Liquid Soap A Challenge for the Formulator," *Household & Personal Products Inds.*, pp. 46-48 (1981).

(Continued)

*Primary Examiner*—Brian P Mruk
(74) *Attorney, Agent, or Firm*—Finnegan, Henderson, Farabow, Garrett & Dunner, LLP

(57) ABSTRACT

The present disclosure relates to a liquid cleansing composition, comprising, in a cosmetically acceptable aqueous medium:

(a) at least one anionic surfactant;
(b) at least one electrolyte,
(c) at least one copolymer of methacrylic acid and of a $C_1$-$C_4$ alkyl acrylate, present in an amount of less than 0.5% by weight of active material, relative to the total weight of the composition. The present disclosure also relates to the use of the compositions in cosmetics or dermatology, such as products for cleansing human keratin materials, for instance the skin, and to their use for improving the stability of the texture of the composition at low temperature.

35 Claims, No Drawings

OTHER PUBLICATIONS

Lundmark, "The Evolution of Liquid Soap", *Cosmetics & Toiletries*, 107:49-53 (1992).
Porter, "Handbook of Surfactants", pp. 117-178 (1991).
French Search Report for FR 0452780 (the Priority Application for U.S. Appl. No. 11/287,300, the present application) dated Jul. 4, 2005.
English Language Derwent Abstract for JP 3-34915, Feb. 14, 1991.
English Language Derwent Abstract for JP 4-169 619, Jun. 17, 1992.
Fragrance Journal, Aug. 25, 2001, Fragrance Journal Ltd., pp. 256, 272-277, 287.
Fragrance Journal, Dec. 15, 2002, vol. 30, No. 12, Fragrance Journal Ltd., p. 109.
English language machine translation of JP 2003-516333 provided by the JPO, May 13, 2003.
Henkel / Cospha Technical Data Sheet, Dehyton K, Register May 6, 1996.
Henkel / Cospha Technical Data Sheet, Texapon N 70, Register Sep. 6, 1996.
Fey Otte, Wörterbuch der Kosmetik, 1997, p. 190, Wissenschaftliche Verlagsgesellschaft mbH Stuttgart.
BF Goodrich Technical Data Sheet, Carbopol AQUA SF-1 Polymer Toxicological Summary, Dec. 2000, TOX-009.
DeGussa Care Specialities Technical Data Shett, TEGO Betain F 50, Nov. 13, 1998.
Noveon Technical Data Sheet, Carbopol Aqua SF-1 Polymer, Jul. 2003, TDS-294.
Poster abstract, IFSCC Conference, Sep. 22-24, 2003, J. Castner, Seoul, Korea.
Dow Corning Corporation Material Safety Data Sheet, Dow Corning 2-8299 Cationic Emulsion, Jun. 21, 2006, Version 1.7.
Noveon Consumer Specialities Technical Data Sheet, Carbopol Aqua SF-1 Polymer, Jul. 2007, TDS-294.

\* cited by examiner

LIQUID CLEANING COMPOSITION COMPRISING AT LEAST ONE ANIONIC SURFACTANT AND ITS USE FOR CLEANSING HUMAN KERATIN MATERIALS

This application claims benefit of U.S. Provisional Application No. 60/634,542, filed Dec. 10, 2004, the contents of which are incorporated herein by reference. This application also claims benefit of priority under 35 U.S.C. §119 to French Patent Application No. 04 52780, filed Nov. 26, 2004, the contents of which are also incorporated herein by reference.

The present disclosure relates to a liquid cleansing composition comprising, in a cosmetically acceptable aqueous medium:

(a) at least one anionic surfactant;

(b) at least one electrolyte, and (c) at least one copolymer of methacrylic acid and of a $C_1$-$C_4$ alkyl acrylate, crosslinked in an amount of less than 0.5% by weight of active material, relative to the total weight of the composition.

The present disclosure also relates to the uses of the disclosed compositions in cosmetics or dermatology, such as products for cleansing human keratin materials, for instance, the skin.

Liquid washing shower compositions, which are generally known as "shower gels" are particularly appreciated by consumers. They may generally be in the form of milk, cream or cream-gel packaged in a tube, a bottle or a pump-dispenser bottle, or as an aerosol foam. These formulations comprise five major families of detergent formulation: (1) those based on lauryl sulfate; (2) those based on α-olefin sulfonate; (3) those based on a mixture of anionic, amphoteric and/or non-ionic synthetic surfactants; (4) soap-based formulations; and (5) mixed formulations based on soaps and synthetic surfactants.

These compositions have been described, for example, in the following documents:

U.S. Pat. Nos. 4,387,040; 4,310,432; and 4,310,433.

*Formulation Technology of Liquid Soaps* by Eugene M. Franck—Cosmetic & Toiletries Vol. 97, pages 49-54 (1982).

*Liquid Soap, a challenge for the formulator* by Roger Hart—Household & Personal Care Products Industry May 1981, pages 46-47;

*Comparison of Detergent Based versus Soap Based Liquid Soaps* by Dennis W. Dyer and Thomas Hassapis—Soap/Cosmetics/Chemical Specialities for July, 1993 pages 36; 38 and 40; and

*The Evolution of Liquid Soap* by Larry Lundmark—Cosmetic & Toiletries Vol. 107, December 1992, pages 49-52.

Liquid shower washing formulations may be desirable because they may have at least one of the following benefits:

they generally have good washing properties and generally produce a creamy, airy and dense lather, which starts quickly, they can be hygienic as a result of their packaging, they can be easy to transport as a result of their packaging, they can be simple and economical to use, they can leave the skin soft and non taut after application and rinsing.

These cleansing compositions for the body and/or the hands, depending on the packaging, can have a consistency and a rheology that are suitable for good handling of the product by the user, and good spreading over the surface of the skin to be washed. They generally contain a thickening system chosen, for example, from electrolytes such as sodium chloride, potassium chloride or potassium sulfate; alkanolamides such as cocamide DEA or cocamide MEA; esters of polyethylene glycol and of stearic monoacid or diacid, for instance polyethylene glycol 6000 distearate or mixtures thereof; thickening polymers, for instance crosslinked acrylic polymers such as the "Carbomer" products or copolymers of the acrylate/$C_1$-$C_{30}$ alkyl acrylate type (e.g., CARBOPOL 1382).

On account of the presence of certain thickeners, certain shower gels currently commercially available can pose difficulties in manufacture. This is the case, for example, for thickeners such as the "Carbomer" products or copolymers of the acrylate/$C_{10}$-$C_{30}$ alkyl acrylate type in powder form. For example, copolymers of the acrylate/$C_{10}$-$C_{30}$ alkyl acrylate type in powder form need, during the industrial manufacture of shower gels comprising them, to be incorporated into cold water and to be mixed for long enough to be completely homogenized in the aqueous phase.

To overcome these implementation problems, one solution is to use an electrolyte as the thickening system. However, it has been found that certain shower gels obtained with this type of thickener can be sensitive to low temperatures (below 20° C.) and that the texture of the product is substantially altered. This heat sensitivity is reflected by an elastic and non-runny texture on leaving the packaging, which makes spreading difficult: the product breaks into pieces that slide over the wet skin.

There is thus still a need in the art to find a liquid body hygiene composition based on suitable detergent surfactants and a suitable thickening system, whose industrial manufacture does not present any implementation problems and/or whose texture does not have the described drawbacks. The thickening system and the washing base used should not alter the washing properties or the quality of the lather, for instance the start of lathering, or affect the cosmetic properties of the product, for instance the sensation of softness on the skin after rinsing.

Liquid detergent compositions containing a copolymer of methacrylic acid and of alkyl acrylate as stabilizer or suspension agent for water-insoluble ingredients such as silicones, fatty substances or nacreous agents are known in the art. Such compositions have been described in Japanese Patent Application Nos. JP 3-34915 and JP 4-169 519, and in International Patent Application Publication No. WO 01/76552. However, the lather qualities and the cosmetic properties obtained with these compositions are still not sufficiently satisfactory.

Example 11 of International Patent Application Publication No. WO 2005/023969 discloses a detergent formulation having the following composition:

| Ingredient | INCI name | Amount in weight % |
|---|---|---|
| Carbopol Aqua SF-1 (30%) | Acrylates copolymer | 0.900 |
| Atlas G-4280 (72%) | PEG-80 sorbitan laurate | 4.580 |
| Tegobetaine L7V (30%) | Cocoamidopropyl betaine | 11.330 |
| Glycerin 917 (99%) | Glycerin | 1.900 |
| Polymer JR-400 | Polyquaternium-10 | 0.140 |
| Dowicil 200 | Quaternium-15 | 0.050 |
| Versene 100 XL | Tetrasodium EDTA | 0.263 |
| Water | Water | qs 100 |

However, this document proposes only a solution to the technical problem of reducing the irritation of the skin and/or the eyes.

The present inventors have discovered, surprisingly, that the technical problems mentioned above can be solved by using (1) a detergent system comprising at least one anionic surfactant, (2) at least one thickening system comprising (i) at least one electrolyte and (ii) at least one crosslinked copolymer of methacrylic acid and of a $C_1$-$C_4$ alkyl acrylate in an amount of less than 0.5% by weight of active material, relative to the total weight of the composition.

Accordingly, one aspect of the present disclosure is thus a liquid cleansing composition, comprising, in a cosmetically acceptable aqueous medium:

(a) at least one anionic surfactant;

(b) at least one electrolyte, (c) at least one crosslinked copolymer of methacrylic acid and of a $C_1$-$C_4$ alkyl acrylate, in an amount of less than 0.5% by weight of active material, relative to the total weight of the composition; with the proviso that the composition is not the same as the formulation as defined in the following table:

| Ingredient | INCI name | Amount in weight % |
|---|---|---|
| Carbopol Aqua SF-1 (30%) | Acrylates copolymer | 0.900 |
| Atlas G-4280 (72%) | PEG-80 sorbitan laurate | 4.580 |
| Tegobetaine L7V (30%) | Cocoamidopropyl betaine | 11.330 |
| Glycerin 917 (99%) | Glycerin | 1.900 |
| Polymer JR-400 | Polyquaternium-10 | 0.140 |
| Dowicil 200 | Quaternium-15 | 0.050 |
| Versene 100 XL | Tetrasodium EDTA | 0.263 |
| Water | Water | qs 100 |

Another aspect of the present disclosure is the cosmetic use of the composition defined above for cleansing and/or removing makeup from keratin materials.

Still another aspect of the present disclosure is a cosmetic process for cleansing soiling residue on human keratin materials, wherein the composition of the present disclosure is applied to the keratin materials, in the presence of water, massaged to form a lather, and the lather formed and the soiling residue are removed by rinsing with water.

The present disclosure also relates to the use of a crosslinked copolymer of methacrylic acid and of a $C_1$-$C_4$ alkyl acrylate as defined above in an amount of less than 0.5% by weight of active material in a liquid cleansing composition comprising, in a cosmetically acceptable aqueous medium, at least one anionic surfactant and at least one electrolyte, to improve the stability of the texture of the composition at low temperature.

As used herein, the term "human keratin materials" is understood to mean the skin (body or facial skin, including the hands, the lips, the eyelids and the scalp), the nails and the integuments, for instance the hair, the eyelashes and the eyebrows.

As used herein, the term "physiologically acceptable medium" is understood to mean a medium that is compatible with the skin, mucous membranes, the scalp, the eyes and/or the hair. Moreover, it can be an aqueous medium, i.e., a medium comprising water, for instance, an amount of water of at least 35% by weight, for example ranging from 35% to 95% by weight, such as from 40% to 80% by weight, relative to the total weight of the composition.

The compositions as disclosed herein are liquid cleansing compositions that are suitable for topical application, for instance, for application to the skin. They can generally be in the form of a gel that may or may not be able to flow under its own weight, i.e., having a viscosity that may range, for example, from 5 poises to 250 poises (0.5 Pa·s to 25 Pa·s) and for example from 35 poises to 200 poises (3.5 Pa·s to 20 Pa·s), the viscosity being measured at 25° C. with a Rheomat 180 measuring machine at 200 $s^{-1}$, this machine being equipped with a different spindle depending on the viscosity, for example a No. 2 spindle for viscosity ranges of less than 7 poises, a No. 3 spindle for viscosity ranges from 2 poises to 40 poises, and a No. 4 spindle for viscosity ranges of greater than 20 poises.

Accordingly, the present disclosure relates to the presence of at least one crosslinked copolymer of methacrylic acid and of a $C_1$-$C_4$ alkyl acrylate in a liquid cleansing composition.

Methacrylic acid can be present in an amount, for example, ranging from 20% to 80% by weight, for instance from 25% to 70% by weight, such as from 35% to 65% by weight, relative to the total weight of the copolymer.

The alkyl acrylate can be present, for example, in an amount ranging from 15% to 80% by weight, for instance from 25% to 75% by weight, such as from 35% to 65% by weight, relative to the total weight of the copolymer. It can be chosen from, for instance, methyl acrylate, ethyl acrylate and butyl acrylate. In one embodiment of the present disclosure, ethyl acrylate is used.

This copolymer can be, for example, partially or totally crosslinked with at least one standard polyethylenically unsaturated crosslinking agent, for instance polyalkenyl ethers of sucrose, or of polyols, diallyl phthalates, divinylbenzene, allyl (meth)acrylate, ethylene glycol di(meth)acrylate, methylenebisacrylamide, trimethylolpropane tri(meth) acrylate, diallyl itaconate, diallyl fumarate, diallyl maleate, zinc (meth)acrylate, and castor oil or polyol derivatives manufactured from unsaturated carboxylic acids. The at least one crosslinking agent can be present in an amount, for example, ranging from 0.01% to 5% by weight, for instance from 0.03% to 3% by weight, for instance from 0.05% to 1% by weight, relative to the total weight of the copolymer.

According to one embodiment of the present disclosure, the at least one copolymer of the present disclosure may be in the form of a dispersion in water. The mean size of the at least one copolymer particles in the dispersion can range from 10 nm to 500 nm, for example, from 20 nm to 200 nm, such as from 50 nm to 150 nm.

The at least one copolymer should ideally not be present in an amount exceeding 0.5% by weight of active material. Beyond this amount, the quality of the lather may begin to be substantially impaired, such as regards the start of lathering and the amount of lather.

The at least one copolymer can be present, for example, in an amount ranging from 0.01% to 0.4% by weight, for instance from 0.1% to 0.3% by weight of active material, relative to the total weight of the composition.

The at least one electrolyte present in the composition can be chosen from, for example, alkali metal salts, for instance sodium chloride, potassium chloride or potassium sulfate. In one embodiment of the present disclosure, sodium chloride is used. The at least one electrolyte can be present in an amount greater than or equal to 0.25%, for instance, ranging from 0.25% to 5%, and such as from 0.5% to 3% by weight, relative to the total weight of the composition.

The compositions according to the present disclosure comprise at least one anionic surfactant.

Non-limiting examples of anionic surfactants that may be used include carboxylates, oxyethylenated and/or non-oxyethylenated alkyl sulfates, sulfonates, alkyl sulfoacetates, phosphates, polypeptides, and anionic derivatives of alkyl polyglucoside, and mixtures thereof.

Non-limiting examples of carboxylates that may be mentioned include:

amido ether carboxylates (AEC), for instance sodium laurylamido ether carboxylate (3 EO) sold under the name Akypo Foam 30® by the company Kao Chemicals;

polyoxyethylenated carboxylic acid salts, for instance oxyethylenated (6 EO) sodium lauryl ether carboxylate (65/25/10 C12-14-16) sold under the name Akypo Soft 45 NV® by the company Kao Chemicals; polyoxyethylenated fatty acids of olive oil and of carboxymethyl, product sold under the name Olivem 400® by the company Biologia E Technologia; oxyethylenated (6 EO) sodium tridecyl ether carboxylate sold under the name Nikkol ECTD-6NEX® by the company Nikkol;

acetates such as sodium 2-(2-hydroxyalkyloxy)acetate sold under the name Beaulight SHAA by the company Sanyo;

alkali metal salts of N-acylamino acids, for instance (1) sarcosinates, such as the sodium lauroyl sarcosinate sold under the name Sarkosyl NL 97® by the company Ciba or under the name Oramix L 30® by the company SEPPIC, the sodium myristoyl sarcosinate sold under the name Nikkol Sarcosinate MN® by the company Nikkol, and the sodium palmitoyl sarcosinate sold under the name Nikkol Sarcosinate PN® by the company Nikkol; (2) alaninates, for instance the sodium N-lauroyl-N-methylamidopropionate sold under the name Sodium Nikkol Alaninate LN 30® by the company Nikkol or under the name Alanone ALE® by the company Kawaken, and the N-lauroyl N-methylalanine triethanolamine sold under the name Alanone ALTA® by the company Kawaken; (3) acylglutamates, for instance the triethanolamine monococoylglutamate sold under the name Acylglutamate CT-12® by the company Ajinomoto, and the triethanolamine lauroylglutamate sold under the name Acylglutamate LT-12® by the company Ajinomoto; (4) aspartates, for instance the mixture of triethanolamine N-lauroyl aspartate and of triethanolamine N-myristoyl aspartate sold under the name Asparack® by the company Mitsubishi; (5) glycinates, for instance the sodium N-cocoylglycinate sold under the names Amilite GCS-12® and Amilite GCK 12 by the company Ajinomoto;

citrates such as the oxyethylenated (9 EO) citric monoester of coco alcohols sold under the name Witconol EC 1129 by the company Goldschmidt;

galacturonates, for instance the sodium dodecyl-D-galactoside uronate sold by the company Soliance;

soaps, which are salts of fatty acids of natural or synthetic origin, salified with at least one mineral or organic base. The fatty chain may comprise from 6 to 22 carbon atoms, such as from 8 to 18 carbon atoms. The at least one mineral or organic base may be chosen from alkali metals or alkaline-earth metals, amino acids and amino alcohols. Non-limiting examples of salts that may be used include the sodium, potassium, magnesium, triethanolamine, N-methylglucamine, lysine and arginine salts. Non-limiting examples of soaps that may be mentioned include the potassium or sodium salts of lauric, myristic, palmitic or stearic acid (sodium or potassium laurate, myristate, palmitate and stearate), and mixtures thereof.

Non-limiting examples of oxyethylenated or non-oxyethylenated alkyl sulfates that may be mentioned include the sodium lauryl ether sulfate (70/30 C12-14) (2.2 EO) sold under the name Sipon AOS 225° by the company Cognis, the ammonium lauryl ether sulfate (70/30 C12-14) (3 EO) sold under the name Sipon LEA 370® by the company Cognis, the ammonium (C12-C14) alkyl ether (9 EO) sulfate sold under the name Rhodapex AB/20® by the company Rhodia Chimie, and the mixture of sodium and magnesium lauryl and oleyl ether sulfate sold under the name Empicol BSD 52 by the company Albright & Wilson.

Further non-limiting examples of sulfonates that may be mentioned include (1) α-olefin sulfonates, for instance the sodium α-olefin sulfonate (C14-16) sold under the name Bioterge AS-40® by the company Stepan, under the names Witconate AOS Protege® and Sulframine AOS PH 12® by the company Witco, the sodium secondary olefin sulfonate sold under the name Hostapur SAS 30® by the company Clariant; (2) isothionates, for instance sodium cocoyl isothionate, such as the product sold under the name Jordapon CI P® by the company Jordan, (3) taurates, for instance the sodium salt of palm kernel oil methyltaurate sold under the name Hostapon CT Paste® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

Non-limiting examples of sulfosuccinates that may be mentioned include the oxyethylenated (3 EO) lauryl alcohol monosulfosuccinate (70/30 C12/C14) sold under the names Setacin 103 Special®, Rewopol SB-FA 30 K 4® by the company Witco, the disodium salt of a C12-C14 alcohol hemisulfosuccinate sold under the name Setacin F Special Paste® by the company Zschimmer Schwarz, the oxyethylenated (2 EO) disodium oleamidosulfosuccinate sold under the name Standapol SH 135® by the company Cognis, and the oxyethylenated (5 EO) laurylamide monosulfosuccinate sold under the name Lebon A-5000® by the company Sanyo.

Non-limiting examples of phosphates that may be mentioned include monoalkyl phosphates and dialkyl phosphates, such as the lauryl monophosphate sold under the name MAP 20® by the company Kao Chemicals, the potassium salt of dodecylphosphoric acid, as a mixture of monoester and diester (mainly diester) sold under the name Crafol AP-31® by the company Cognis, the mixture of octylphosphoric acid monoester and diester sold under the name Crafol AP-20® by the company Cognis, and the mixture of ethoxylated (7 mole of EO) 2-butyloctanol phosphoric monoester and diester sold under the name Isofol 127 EO Phosphate Ester® by the company Condea.

Non-limiting examples of polypeptides (which are compounds obtained by condensing a fatty chain onto cereal, such as wheat and oat, amino acids) that may be mentioned include the potassium salt of hydrolysed lauroyl wheat protein sold under the name Aminofoam W OR® by the company Croda; the triethanolamine salt of hydrolysed cocoyl soybean protein sold under the name May-Tein SY® by the company Maybrook; the sodium salt of oat lauroyl amino acids sold under the name Proteol Oat® by the company SEPPIC; collagen hydrolysate grafted onto coconut fatty acid, sold under the name Geliderm 3000® by the company Deutsche Gelatine; and soybean proteins acylated with hydrogenated coconut acids, sold under the name Proteol VS 22® by the company SEPPIC.

In one embodiment of the present disclosure, the anionic alkyl polyglucoside derivatives are chosen from glyceryl citrates, tartrates, sulfosuccinates, carbonates and ethers obtained from alkyl polyglucosides. Non-limiting examples that may be mentioned include the sodium salt of cocoylpolyglucoside (1,4) tartaric ester, sold under the name Eucarol AGE-ET® by the company Cesalpinia; the disodium salt of cocoylpolyglucoside (1,4) sulfosuccinic ester, sold under the name Essai 512 MP® by the company SEPPIC; the sodium salt of cocoylpolyglucoside (1,4) citric ester sold under the name Eucarol AGE-EC® by the company Cesalpinia, and the sodium lauryl polyglucoside ether carboxylate sold under the name Plantapon LGC Sorb by the company Cognis.

$C_6$-$C_{24}$ alkyl ether sulfate salts comprising from 1 to 30 ethylene oxide groups can be used, for example, the alkali metal or alkaline-earth metal, ammonium, amine or amino alcohol salts, and for instance, the sodium salts such as oxyethylenated sodium ($C_{12}$-$C_{14}$)alkyl ether sulfates comprising a mean number of ethylene oxide groups ranging from 1 to 4, and for example, sodium laureth sulfate (CTFA name).

According to one embodiment of the present disclosure, the compositions also comprise at least one amphoteric or zwitterionic surfactant.

Non-limiting examples of amphoteric and zwitterionic surfactants that may be used include alkylbetaines, N-alkylamidobetaines and derivatives thereof, sultaines, alkylpolyaminocarboxylates (APAC) and alkyl amphoacetates, and mixtures thereof.

Non-limiting examples of alkylbetaines that may be mentioned include cocobetaine, for instance the product sold under the name Dehyton AB-30® by the company Cognis; laurylbetaine, for instance the product sold under the name Genagen KB® by the company Clariant; oxyethylenated (10 EO) laurylbetaine, for instance the product sold under the name Lauryl Ether (10 OE) Betaine® by the company Shin Nihon Rica; oxyethylenated (10 EO) stearylbetaine, for instance the product sold under the name Stearyl Ether (10 OE) Betaine® by the company Shin Nihon Rica.

Among the N-alkylamidobetaines and derivatives thereof that may be mentioned, by way of non-limiting example, are the cocamidopropylbetaine sold under the name Lebon 2000 HG® by the company Sanyo or under the name Empigen BB® by the company Albright & Wilson; the lauramidopropylbetaine sold under the name Rewoteric AMB12P® by the company Witco.

A sultaine that may be mentioned, by way of non-limiting example, is the cocoylamidopropylhydroxysulfobetaine sold under the name Crosultaine C-50® by the company Croda.

Alkylpolyaminocarboxylates (APAC) that may be mentioned, by way of non-limiting example include the sodium cocoylpolyaminocarboxylate sold under the name Ampholak 7 CX/C® and Ampholak 7 CX® by the company Akzo Nobel; the sodium stearylpolyaminocarboxylate sold under the name Ampholak 7 TX/C® by the company Akzo Nobel; the sodium carboxymethyloleylpolypropylamine sold under the name Ampholak XO7/C® by the company Akzo Nobel.

Non-limiting examples of alkylamphoacetates that may be mentioned include N-disodium N-cocoyl-N-carboxymethoxyethyl-N-carboxymethylethylenediamine (CTFA name: disodium cocamphodiacetate), for instance the product sold under the name Miranol C2M Concentrate NP® by the company Rhodia Chimie; and N-sodium N-cocoyl-N-hydroxyethyl-N-carboxymethylethylenediamine (CTFA name: sodium cocamphoacetate).

In one embodiment of the present disclosure, the at least one amphoteric surfactant is chosen from:

cocobetaine such as the commercial products Miratraine BB/FLA from Rhodia or Empigen BB/FL from Huntsman, and disodium cocoamphodiacetate, for instance the product sold under the trade name Miranol® C2M Concentrate by the company Rhodia.

The compositions according to the present disclosure may also comprise at least one nonionic surfactant. These are compounds that are well known per se (see, in this regard, for example, "Handbook of Surfactants" by M. R. Porter, published by Blackie & Son (Glasgow and London), 1991, pp 116-178). Thus, the at least one non-ionic surfactant may be chosen from, for example, polyethoxylated, polypropoxylated and polyglycerolated fatty alcohols, fatty α-diols, fatty alkylphenols and fatty acids, having a fatty chain comprising, for example, from 8 to 18 carbon atoms, the number of ethylene oxide or propylene oxide groups possibly ranging, for instance, from 2 to 50, and the number of glycerol groups ranging, for example, from 2 to 30. Maltose derivatives may also be mentioned. Non-limiting mention may also be made of copolymers of ethylene oxide and of propylene oxide, condensates of ethylene oxide and of propylene oxide with fatty alcohols; polyethoxylated fatty amides comprising, for instance, from 2 to 30 mol of ethylene oxide, polyglycerolated fatty amides comprising, for example from 1 to 5, such as from 1.5 to 4, glycerol groups; polyethoxylated fatty amines comprising, for example, from 2 mol to 30 mol of ethylene oxide; ethoxylated fatty acid esters of sorbitan comprising, for instance, from 2 mol to 30 mol of ethylene oxide; fatty acid esters of sucrose, fatty acid esters of polyethylene glycol, ($C_6$-$C_{24}$)alkylpolyglycosides, N—($C_6$-$C_{24}$)alkylglucamine derivatives, and amine oxides such as ($C_{10}$-$C_{14}$)alkylamine oxides or N—($C_{10}$-$C_{14}$)acylaminopropylmorpholine oxides; and mixtures thereof.

Among the alkylpolyglucosides that may be used, non-limiting mention may be made of those comprising an alkyl group comprising from 6 to 30 carbon atoms, such as from 8 to 16 carbon atoms, and comprising a hydrophilic group (glucoside) for instance comprising from 1.2 to 3 saccharide units. Non-limiting examples of alkylpolyglucosides that may be mentioned include decylglucoside (alkyl-C9/C11-polyglucoside (1.4)), for instance the product sold under the name Mydol 10® by the company Kao Chemicals, under the name Plantaren 2000 UP® by the company Cognis, and under the name Oramix NS 10® by the company SEPPIC; caprylyl/capryl glucoside, for instance the product sold under the name Oramix CG 11® by the company SEPPIC; laurylglucoside, for instance the products sold under the names Plantaren 1200 N® and Plantacare 1200® by the company Cognis; and the cocoglucoside, for instance the product sold under the name Plantacare 818/UP® by the company Cognis.

The maltose derivatives can be, for example, those described in European Patent Application Publication No. EP-A-566 438, such as O-octanoyl-6'-D-maltose or O-dodecanoyl-6'-D-maltose described in French Patent Application Publication No. FR-2 739 556.

Among the polyglycerolated fatty alcohols that may be used, non-limiting mention may be made of polyglycerolated dodecanediol (3.5 mol of glycerol), such as the product manufactured under the name Chimexane NF® by the company Chimex.

The cleansing composition according to the present disclosure is a foaming detergent composition, and it comprises at least one anionic surfactant that gives the composition the foaming nature. It may also additionally comprise at least one other surfactant chosen from nonionic, amphoteric and zwitterionic surfactants.

The total amount of the at least one surfactant, in a total amount of surfactants by weight of active material, can be greater than or equal to 5% by weight. It can range, for example, from 5% to 50% by weight, for instance from 6% to 50% by weight, such as from 6% to 30% by weight, and from 8% to 25% by weight, relative to the total weight of the composition.

The cosmetically acceptable aqueous medium of the compositions of the present disclosure may comprise, besides water, at least one solvent chosen from lower alcohols comprising from 1 to 6 carbon atoms, such as ethanol; polyols such as glycerol; glycols, for instance butylene glycol, isoprene glycol, propylene glycol, polyethylene glycols such as PEG-8; sorbitol; sugars such as glucose, fructose, maltose, lactose and sucrose; and mixtures thereof. The at least one solvent can be present in the composition of the present disclosure in an amount ranging from 0.5% to 30% by weight, for instance from 5% to 20% by weight, relative to the total weight of the composition. In one embodiment of the present disclosure, the composition comprises from 50% to 95% by weight of water, relative to the total weight of the composition.

The compositions of the present disclosure may also comprise, for example, at least one cationic polymer of the polyquaternium type, which give the foaming composition softness and creaminess.

The at least one cationic polymer may be chosen from, by way of non-limiting example, the following polymers:

Polyquaternium 5, such as the product Merquat 5 sold by the company Calgon;

Polyquaternium 6, such as the product Salcare SC 30 sold by the company Ciba, and the product Merquat 100 sold by the company Calgon;

Polyquaternium 7, such as the products Merquat S, Merquat 2200 and Merquat 550 sold by the company Calgon; and the product Salcare SC 10 sold by the company Ciba;

Polyquaternium 10, such as the product Polymer JR400 sold by the company Amerchol;

Polyquaternium 11, such as the products Gafquat 755, Gafquat 775N and Gafquat 734 sold by the company ISP;

Polyquaternium 15, such as the product Rohagit KF 720 F sold by the company Rohm;

Polyquaternium 16, such as the products Luviquat FC905, Luviquat FC370, Luviquat HM552 and Luviquat FC550 sold by the company BASF;

Polyquaternium 22, such as the product Merquat 280 sold by the company Calgon;

Polyquaternium 28, such as the product Styleze CC10 sold by the company ISP;

Polyquaternium 39, such as the product Merquat Plus 3330 sold by the company Calgon;

Polyquaternium 44, such as the product Luviquat Care sold by the company BASF;

Polyquaternium 46, such as the product Luviquat Hold sold by the company BASF; and Polyquaternium 47, such as the product Merquat 2001 sold by the company Calgon.

Cationic polymers that may also be used include cationic guars, such as the product Jaguar sold by the company Rhodia.

The composition of the present disclosure may also comprise at least one adjuvant usually used in cosmetics, such as those used in cleansing products. Non-limiting examples of adjuvants that may be mentioned include fragrances, preserving agents, sequestering agents (EDTA), pigments, nacreous agents or opacifiers, mineral or organic fillers, matting agents, bleaching agents or exfoliants, soluble dyes, cosmetic or dermatological active agents, nonionic polymers such as polyvinylpyrrolidone (PVP), anionic polymers and fatty substances that are incompatible with the aqueous medium, for instance oils or waxes. The at least one adjuvant can be present in the composition, in a total amount, for example, ranging from 0.01% to 20% by weight, relative to the total weight of the composition. These adjuvants and the concentrations thereof should be such that they do not modify the property desired for the composition of the present disclosure.

Non-limiting examples of oils that may be mentioned include oils of plant origin (jojoba oil, avocado oil, sesame oil, sunflower oil, corn oil, soybean oil, safflower oil or grapeseed oil), mineral oils (petroleum jelly or optionally hydrogenated isoparaffins), synthetic oils (isopropyl myristate, cetearyl octanoate, polyisobutylene, ethylhexyl palmitate or alkylbenzoates), volatile or non-volatile silicone oils such as polydimethylsiloxanes (PDMS) and cyclodimethoxylsiloxanes or cyclomethicones, and fluoro oils or fluorosilicone oils, and also mixtures of these oils.

At least one active agent may also be used in the composition of the present disclosure, including, by way of non-limiting example, any active agent usually used in cosmetics and dermatology, for instance water-soluble or liposoluble vitamins or provitamins, for instance vitamin A (retinol), vitamin C (ascorbic acid), vitamin B3 or PP (niacinamide), vitamin B5 (panthenol), vitamin E (tocopherol), vitamin K1, β-carotene, and derivatives of these vitamins such as esters thereof; steroids, for instance DHEA and 7α-hydroxy DHEA; antiseptic agents; anti-seborrhoeic agents and antimicrobial agents such as benzoyl peroxide, salicylic acid, triclosan, tricarban or azelaic acid; moisturizers, for instance glycerol, hyaluronic acid, pyrrolidonecarboxylic acid (PCA) and its salts, sodium pidolate, serine, xylitol, trehalose, ectoin, ceramides or urea; keratolytic agents and anti-ageing agents such as α-hydroxy acids, for instance glycolic acid, citric acid or lactic acid, β-hydroxy acids, for instance salicylic acid and its derivatives; enzymes and coenzymes, such as coenzyme Q10; sunscreens; optical brighteners; slimming active agents, for instance caffeine, theophylline or theobromine; anti-inflammatory agents such as 18 β-glycyrrhetinic acid and ursolic acid, and mixtures thereof. A mixture of two or more of these active agents may be used. The at least one active agent can be present, for example in an total amount for all active agents, ranging from 0.01% to 20%, for instance, from 0.1% to 10%, such as from 0.5% to 5% by weight, relative to the total weight of the composition.

Among the fillers that may be used, non-limiting mention may be made of mineral fillers such as talc or magnesium silicate (particle size: 5 microns) sold under the name Luzenac 15 M00® by the company Luzenac; kaolin or aluminium silicate, for instance the product sold under the name Kaolin Supreme® by the company Imerys; organic fillers such as starch, for instance the product sold under the name Amidon de Maïs B® by the company Roquette; Nylon microspheres, for instance those sold under the name Orgasol 2002 UD NAT COS® by the company Atochem; expanded microspheres based on vinylidene chloride/acrylonitrile/methacrylonitrile copolymer comprising isobutane, for instance those sold under the name Expancel 551 DE® by the company Expancel.

At least one fiber may also be added to the composition of the present disclosure, for instance Nylon fibers (Polyamide 0.9 Dtex 0.3 MM sold by the company Etablissements Paul Bonte) and cellulose or "Rayon" fibers (Rayon Flock RCISE NOOO3 MO4® sold by the company Claremont Flock Corporation).

Among the nacreous agents or opacifiers that may be used, non-limiting mention may be made of sodium or magnesium palmitates, sodium or magnesium stearates and hydroxystearates, fatty-chain acyl derivatives such as ethylene glycol or polyethylene glycol monostearates or distearates, fatty-chain ethers, for instance distearyl ether or 1-(hexadecyloxy)-2-octadecanol, and fatty alcohols, such as stearyl alcohol, cetyl alcohol or behenyl alcohol, and mixtures thereof.

The foaming compositions according to the present disclosure may be used in cosmetics and dermatology, and they may, for example, be a cosmetic composition, such as products for cleansing or removing makeup from the skin (body, face and/or eyes), the scalp and/or the hair. They may be used for any type of skin (dry, normal, combination or greasy skin).

The compositions of the present disclosure may be used, for instance as shower products; bath products; hand cleansing products; shampoos; products for removing makeup from the eyes and/or the face.

Thus, one embodiment of the present disclosure is a process for cleansing and/or removing makeup from human keratin materials, such as the skin, comprising applying a product comprising a composition as disclosed herein.

The compositions according to the present disclosure may also be used for treating greasy skin, for example by adding thereto specific active agents for treating greasy skin, such as anti-seborrhoeic agents, for instance salicylic acid and its derivatives, azelaic acid, triclosan, tricarban, piroctone olamine or niacinamide (vitamin PP).

Thus, another embodiment of the present disclosure is a process for treating greasy skin using a composition as disclosed herein, and also a process for the preparation of a composition for treating greasy skin.

The compositions according to the present disclosure can have a final pH ranging from 3 to 10. For example, the pH can range from 4 to 8. The pH may be adjusted to the desired value conventionally by adding at least one base (organic or mineral) to the composition, for example aqueous ammonia or a primary, secondary or tertiary (poly)amine, for instance monoethanolamine, diethanolamine, triethanolamine, isopropanolamine or 1,3-propanediamine, or alternatively by adding at least one mineral and/or organic acid, such as a carboxylic acid, for instance citric acid.

The compositions of the present disclosure may be packaged, according to the chosen application, in the form of a bottle, a tube, a pump-dispenser bottle, an aerosol device or any other packaging mode that is suitable for a liquid washing composition.

The cleansing compositions of the present invention packaged in aerosol devices may comprise at least one propellant usually used for the preparation of aerosol compositions. Non-limiting mention may be made, for example, of hydrocarbon-based gases, for instance propane, n-butane or isobutane, and mixtures thereof; fluorinated gases, for instance chlorodifluoromethane, dichlorodifluoromethane, difluoroethane, chlorodifluoroethane, dichlorotetrafluoroethane, etc. and mixtures thereof; hydrofluorocarbon-based gases; dimethyl ether and mixtures of dimethyl ether with at least one hydrocarbon-based gas; nitrogen, air, and carbon dioxide and mixtures thereof may also be used as propellant gases in the present invention. Hydrocarbon-based gases comprising from 2 to 6 carbon atoms, such as an isobutane, propane and n-butane mixture, are used in one embodiment of the present disclosure. The at least one propellant gas can be present in the device, in a total amount, ranging from 0.1% to 15% by weight, such as ranging from 1% to 8% by weight, relative to the total weight of the composition.

Another embodiment of the present disclosure is a method of improving the stability of the texture of the a composition at a low temperature, comprising adding to a composition at least one crosslinked or non-crosslinked copolymer of methacrylic acid and of a $C_1$-$C_4$ alkyl acrylate in a liquid cleansing composition comprising, in a cosmetically acceptable aqueous medium, at least one anionic surfactant and at least one electrolyte.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The examples that follow serve to illustrate the present disclosure without, however, being limiting in nature. The amounts indicated are weight percentages, unless otherwise mentioned, and the names of the compounds are given as chemical names or CTFA names (International Cosmetic Ingredient Dictionary and Handbook), depending on the case.

EXAMPLES

|  | Example 1 (% by weight of AM) Inventive Composition | Example 2 (% by weight of AM) Inventive Composition | Example 3 (% by weight of AM) Comparative Example | Example 4 (% by weight of AM) Comparative Example |
|---|---|---|---|---|
| Sodium laureth sulfate | 9.80 | 9.80 | 9.80 | 9.80 |
| Sodium chloride | 2.16 | 2.16 | 2.16 | 2.16 |
| Cocobetaine | 1.9875 | 1.9875 | 1.9875 | 1.9875 |
| Glycerin | 1 | 1 | 1 | 1 |
| Hexylene glycol | 1 | 1 | 1 | 1 |
| Glycol distearate | 1 | 1 | 1 | 1 |
| Disodium cocoamphodiacetate | 0.6 | 0.6 | 0.6 | 0.6 |
| Disodium EDTA | 0.26 | 0.26 | 0.26 | 0.26 |
| Acrylates copolymer | 0.24 | 0.399 | 0.6 | 0 |
| Sodium glycolate | 0.12 | 0.12 | 0.12 | 0.12 |
| Polyquaternium-7 | 0.11 | 0.11 | 0.11 | 0.11 |

-continued

|  | Example 1 (% by weight of AM) Inventive Composition | Example 2 (% by weight of AM) Inventive Composition | Example 3 (% by weight of AM) Comparative Example | Example 4 (% by weight of AM) Comparative Example |
| --- | --- | --- | --- | --- |
| Preserving agents | qs | qs | qs | Qs |
| Fragrance | qs | Qs | qs | Qs |
| Water | 82.8122 | 82.6532 | 82.4522 | 83.0522 |

The compositions were prepared according to the following procedure:

1) In the manufacturing tank:
  first introduced were the water, the preserving agents and the glycerol
  then added, with slower stirring, some of the sodium laureth sulfate until fully dissolved,
  next, added successively, with stirring, the disodium EDTA, the polyquaternium-7, the acrylates copolymer and the fragrance.

2) The glycol distearate was melted with some of the water and some of the sodium laureth sulfate.

3) This preparation was added, followed by the cocobetaine and the disodium cocoamphodiacetate to the manufacturing tank.

The compositions had good foaming and washing properties; they did not dry out the skin and left a sensation of softness after rinsing. No elastic texture upon leaving the packaging was observed when the composition was stored at a temperature of about 15° C.-18° C.

The observation of the elastic texture was made from a sensory point of view, as described below:

2 g of product was weighed in a dish and placed at 4° C. for 15 minutes, after this time, the product was tapped with a spatula: if the appearance was elastic and gelatinous, the texture of the product was unacceptable.

This observation was made for the formulations corresponding to Examples 1 to 4:

Examples 1 and 2 comprising the acrylate copolymer in an amount of less than 0.5% by weight of active material had an acceptable texture: the appearance in the dish was not elastic or gelatinous, but runny.

Comparative Example 3 comprising the acrylate copolymer in an amount of greater than 0.5% by weight had unsatisfactory cosmetic qualities, such as the start of lathering and the amount of lather.

Comparative Example 4 not comprising the acrylate copolymer had an unacceptable texture: the appearance in the dish was elastic and gelatinous.

What is claimed is:

1. A liquid cleansing composition comprising, in a cosmetically acceptable aqueous medium:
  (a) at least one anionic surfactant;
  (b) from 0.5 to 3% by weight of NaCl; and
  (c) at least one crosslinked copolymer of methacrylic acid and of a $C_1$-$C_4$ alkyl acrylate, in an amount ranging from 0.01 to 0.4% by weight of active material, relative to the total weight of the composition.

2. The liquid cleansing composition according to claim 1, wherein, in the at least one copolymer, the methacrylic acid is present in an amount ranging from 20% to 80% by weight, relative to the total weight of the copolymer.

3. The liquid cleansing composition according to claim 2, wherein, in the at least one copolymer, the methacrylic acid is present in an amount ranging from 35% to 65% by weight, relative to the total weight of the copolymer.

4. The liquid cleansing composition according to claim 1, wherein, in the at least one copolymer, the alkyl acrylate is present in an amount ranging from 15% to 80% by weight, relative to the total weight of the copolymer.

5. The liquid cleansing composition according to claim 4, wherein, in the at least one copolymer, the alkyl acrylate is present in an amount ranging from 35% to 65% by weight, relative to the total weight of the copolymer.

6. The liquid cleansing composition according to claim 1, wherein, in the at least one copolymer, the alkyl acrylate is chosen from methyl acrylate, ethyl acrylate and butyl acrylate.

7. The liquid cleansing composition according to claim 6, wherein the alkyl acrylate is ethyl acrylate.

8. The liquid cleansing composition according to claim 1, wherein the at least one crosslinked copolymer of methacrylic acid and of a $C_1$-$C_4$ alkyl acrylate is partially or totally crosslinked with at least one standard polyethylenically unsaturated crosslinking agent.

9. The liquid cleansing composition according to claim 8, wherein the at least one crosslinking agent is present in an amount ranging from 0.01% to 5% by weight, relative to the total weight of the copolymer.

10. The liquid cleansing composition according to claim 9, wherein the at least one crosslinking agent is present in an amount ranging from 0.05% to 1% by weight, relative to the total weight of the copolymer.

11. The liquid cleansing composition according to claim 1, wherein the at least one copolymer of methacrylic acid and of a $C_1$-$C_4$ alkyl acrylate is in the form of a dispersion of particles in water.

12. The liquid cleansing composition according to claim 11, wherein the mean size of the particles of the at least one copolymer in the dispersion ranges from 10 nm to 500 nm.

13. The liquid cleansing composition according to claim 12, wherein the mean size of the particles of the at least one copolymer in the dispersion ranges from 50 nm to 150 nm.

14. The liquid cleansing composition according to claim 1, wherein the at least one copolymer of methacrylic acid and of a $C_1$-$C_4$ alkyl acrylate is the crosslinked methacrylic acid/ethyl acrylate copolymer in the form of an aqueous 30% dispersion.

15. The liquid cleansing composition according to claim 1, wherein the at least one copolymer of methacrylic acid and of a $C_1$-$C_4$ alkyl acrylate is present in an amount ranging from 0.1% to 0.3% by weight of active material, relative to the total weight of the composition.

16. The liquid cleansing composition according to claim 1, wherein the at least one anionic surfactant is chosen from carboxylates; oxyethylenated and non-oxyethylenated alkyl sulfates; sulfonates; alkyl sulfoacetates; phosphates; polypeptides; and anionic derivatives of alkyl polyglucoside.

17. The liquid cleansing composition according to claim 16, wherein the at least one anionic surfactant is chosen from $C_6$-$C_{24}$ alkyl ether sulfate salts comprising from 1 to 30 ethylene oxide groups.

18. The liquid cleansing composition according to claim 17, wherein the at least one anionic surfactant is chosen from oxyethylenated sodium ($C_{12}$-$C_{14}$)alkyl ether sulfates comprising a mean number of ethylene oxide groups ranging from 1 to 4.

19. The liquid cleansing composition according to claim 18, wherein the at least one anionic surfactant is sodium laureth sulfate.

20. The liquid cleansing composition according to claim 1, further comprising at least one surfactant chosen from amphoteric and zwitterionic surfactants.

21. The liquid cleansing composition according to claim 20, wherein the at least one surfactant chosen from amphoteric and zwitterionic surfactants is chosen from alkylbetaines, N-alkylamidobetaines and derivatives thereof, sultaines, alkylpolyaminocarboxylates and alkylamphoacetates.

22. The liquid cleansing composition according to claim 21, in which the at least one surfactant chosen from amphoteric and zwitterionic surfactants is chosen from:
cocobetaine, and
disodium cocoamphodiacetate.

23. The liquid cleansing composition according to claim 1, further comprising at least one nonionic surfactant.

24. The liquid cleansing Composition according to claim 23, wherein the at least one nonionic surfactant is chosen from:
polyethoxylated, polypropoxylated and polyglycerolated fatty alcohols, fatty α-diols, fatty alkylphenols and fatty acids, comprising a fatty chain;
copolymers of ethylene oxide and of propylene oxide,
condensates of ethylene oxide and of propylene oxide with fatty alcohols;
polyethoxylated fatty amides,
polyglycerolated fatty amides,
polyethoxylated fatty amines,
ethoxylated fatty acid esters of sorbitan,
fatty acid esters of sucrose,
fatty acid esters of polyethylene glycol,
($C_6$-$C_{24}$) alkylpolyglycosides,
N—($C_6$-$C_{24}$)alkylglucamine derivatives,
amine oxides, and
N—($C_{10}$-$C_{14}$)acylaminopropylmorpholine oxides.

25. The liquid cleansing composition according to claim 1, wherein the at least one surfactant, in a total amount of all possible surfactant(s), is present in an amount by weight of active material greater than or equal to 5% by weight relative to the total weight of the composition.

26. The liquid cleansing composition according to claim 25, wherein the at least one surfactant, in a total amount of all possible surfactant(s), is present in an amount by weight of active material ranging from 5% to 50% by weight, relative to the total weight of the composition.

27. The liquid cleansing composition according to claim 25, wherein the at least one surfactant, in a total amount of all possible surfactant(s), is present in an amount by weight of active material ranging from 8% to 25% by weight, relative to the total weight of the composition.

28. The liquid cleansing composition according to claim 1, further comprising at least one cationic polymer.

29. The liquid cleansing composition according to claim 1, further comprising at least one cosmetic adjuvant chosen from fragrances, preserving agents, sequestering agents (EDTA), pigments, nacreous agents, opacifiers, mineral and organic fillers, matting agents, bleaching agents, exfoliants, soluble dyes, cosmetic and dermatological active agents, nonionic polymers, anionic polymers and fatty substances.

30. A cosmetic process for cleansing and/or removing makeup from human keratin materials comprising applying a product to the human keratin materials comprising, in a cosmetically acceptable aqueous medium:
(a) at least one anionic surfactant;
(b) from 0.5 to 3% by weight of NaCl; and
(c) at least one crosslinked copolymer of methacrylic acid and of a $C_1$-$C_4$ alkyl acrylate, in an amount ranging from 0.01 to 0.4% by weight of active material, relative to the total weight of the composition.

31. The liquid cleansing composition according to claim 1, wherein it is in the form of bath or shower product, a product for cleansing the hands, a shampoo, and/or a product for removing makeup from the eyes, the face and/or the lips.

32. The liquid cleansing composition according to claim 1, further comprising at least one active agent for treating greasy skin chosen from anti-seborrhoeic agents.

33. A process for preparing a formulation for treating greasy skin, comprising:
adding, to a composition comprising, in a cosmetically acceptable medium, at least one anionic surfactant; from 0.5 to 3% by weight of NaCl; and at least one crosslinked copolymer of methacrylic acid and of a $C_1$-$C_4$ alkyl acrylate, in an amount ranging from 0.01 to 0.4% by weight of active material, at least one active agent for treating greasy skin chosen from anti-seborrhoeic agents.

34. A cosmetic process for cleansing soiling residue from human keratin materials, comprising
applying to the keratin materials, in the presence of water, a composition comprising, in a cosmetically acceptable aqueous medium:
(a) at least one anionic surfactant;
(b) from 0.5 to 3% by weight of NaCl; and
(c) at least one crosslinked copolymer of methacrylic acid and of a $C_1$-$C_4$ alkyl acrylate, in an amount ranging from 0.01 to 0.4% by weight of active material, relative to the total weight of the composition
massaging the composition to form a lather and
removing the lather formed and the soiling residue by rinsing with water.

35. A process for improving the stability of the texture of a liquid cleansing composition comprising adding to the liquid cleansing composition a composition comprising, in a cosmetically acceptable medium, at least one crosslinked copolymer of methacrylic acid and of a $C_1$-$C_4$ alkyl acrylate, in an amount ranging from 0.01 to 0.4% by weight of active material, at least one anionic surfactant and from 0.5 to 3% by weight of NaCl.

* * * * *